United States Patent [19]

Tanaka et al.

[11] Patent Number: 5,608,058

[45] Date of Patent: Mar. 4, 1997

[54] PROCESSING FOR PURIFYING CROWN COMPOUNDS

[75] Inventors: Shinri Tanaka; Yasuhiko Kawashima, both of Tokyo, Japan

[73] Assignee: Konica Corporation, Tokyo, Japan

[21] Appl. No.: 189,700

[22] Filed: Feb. 1, 1994

[30] Foreign Application Priority Data

Feb. 18, 1993 [JP] Japan .................................. 5-029313

[51] Int. Cl.$^6$ ..................... C07D 267/22; C07D 323/00; C07D 321/12
[52] U.S. Cl. .......................... 540/454; 540/456; 540/467; 540/468; 540/469; 549/11; 549/348; 549/351; 549/352; 549/353
[58] Field of Search ................................... 549/352, 353, 549/348, 11, 351; 540/467, 468, 469, 454, 456

[56] References Cited

PUBLICATIONS

Chemical Abstracts, vol. 117, No. 28, 1992, Columbus, Ohio, US; abstract No. 90337b, p. 789, col. 1.
Chemical Abstracts, vol. 101, No. 7, 1984, Columbus, Ohio, US; abstract No. 55121z, p. 626; col. 2.
European Search Report, completed May 17, 1994 by Examiner J. Francois at The Hague.

*Primary Examiner*—C. Warren Ivy
*Assistant Examiner*—Raymond Covington
*Attorney, Agent, or Firm*—Finnegan, Henderson, Farabow, Garrett & Dunner, L.L.P.

[57] ABSTRACT

A process of preparing a purified crown compound is disclosed which comprises the steps of (a) dissolving a crown compound and a salt in an organic solvent to form a solution of a complex salt of a crown compound; (b) filtering the solution to obtain a filtrate; (c) adding water to the filtrate to produce a precipitate; and (d) filtering out the produced precipitate.

10 Claims, No Drawings

PROCESSING FOR PURIFYING CROWN COMPOUNDS

FIELD OF THE INVENTION

The present invention relates to a process for purifying a crown compound.

BACKGROUND OF THE INVENTION

Crown compounds have found extensive applications such as phase transfer catalysts for organic syntheses, selective capture and separation of metal ions, resolution of optical isomers of amino acids, uses in ion selective electrodes, and uses in pharmaceuticals, agricultural chemicals, photographic emulsions, etc.

To facilitate the use of crown compounds in these areas, it is desired that highly purified crown compounds be able to be obtained more easily at cheaper prices.

As processes for synthesizing crown compounds, those described in J. Am. Chem. Soc. Vol. 89, p. 7017 (1967), for example, are known; however, there are no description on any purification process capable of providing a crown compound of adequate purity. Organic Syntheses, vol. 52, p. 66 (1972) describes a process for recrystallizing crown compounds from benzene or dioxane, but the process shown therein has disadvantages such as inabilities of providing an adequate purity or a high yield, use of toxic solvents, high costs, etc.

Further, crown compounds include those which are liquid at ordinary temperature and can be hardly purified by recrystallization, an example of which is 15-crown-5. Crown compounds are relatively stable to heat and may be purified by distillation; but, distillation of ethers such as crown compounds on an industrial scale is not favorable because ethers are liable to yield explosive peroxides when contacted with air at high temperature.

As described above, there has not been found so far any process capable of purifying safely and efficiently crown compounds which are liquid at ordinary temperature; therefore, development of such a process is desired.

SUMMARY OF THE INVENTION

Accordingly, an object of the present invention is to provide a process for purifying crown compounds which can give pure crown compounds cheaply, easily and efficiently.

The above problem is solved by a process of preparing a purified crown compound comprising the steps of:

(a) dissolving a crown compound and a salt in an organic solvent to form a solution of a complex salt of a crown compound;

(b) purifying the solution; and (c) adding water to the purified solution

DETAILED DESCRIPTION OF THE INVENTION

The invention is hereinafter described in detail.

The term "crown compound" used in the invention means a large cyclic compound having, as an electron-donating atom, a heteroatom such as an oxygen, nitrogen or sulfur atom in the ring structure and having a function to capture a cation in the hole of the ring structure. The crown compound includes heterocyclic compounds having two or more heterocyclic rings.

The crown compound, to which the invention is applied, is preferably a crown ether, more preferably a crown ether having a 12- to 24-membered ring, and most preferably a crown ether having a 15- to 21-membered ring.

The salts used to form a complex of a crown compound include a salt of an element belonging to a IA group (e.g., Li, Na, K, Rb or Cs), IB group (e.g., Ag or Au), IIA group (e.g., Ca, Sr or Ba), IIB group (e.g., Cd or Hg), IIIA group (e.g., La or Ce), IIIB group (e.g., Tl) or IVB group (e.g., Pb) of the Periodic Table, as well as an ammonium salt including $NH^{4+}$ or $RNH^{3+}$ (wherein R represents an alkyl group or an aryl group).

The anionic component of the salt is not particularly limited in chemical structure; but, it is preferred that a best one be selected by taking into accounts the solubility of a salt used, the solubility of a crown compound's complex formed and the stability of the complex. Examples of useful salts include potassium acetate, sodium acetate, ammonium acetate, lithium chloride, silver thiocyanate, sodium thiocyanate and potassium thiocyanate.

The term "purification" is intended to include the usual purification processes such as recrystallization, treatment with active carbon, and separation of insoluble matters by filtration. Conducting separation of insoluble matters by filtration is especially effective in the embodiment of the invention.

The organic solvent used in the invention can be properly selected, without particular limitation, from ones of which characteristics are suitable for the purification. Such an organic solvent may be either miscible with water or immiscible with water. In view of the solubility of the crown compound's complex according to the invention, use of an alcohol-type solvent such as methanol, ethanol, n-propanol, n-butanol or i-propanol is preferred.

Taking operability, solvent removal and drying into consideration, preferred is a solvent having a melting point of 30° C. to 150° C. under 1 atm.

The following are examples of the crown compound to which the present invention can be applied, but the scope of the invention is by no means limited to them.

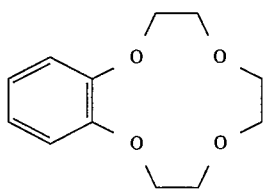

S-1

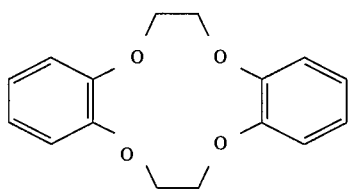

S-2

-continued
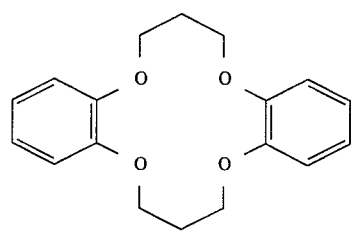
S-3
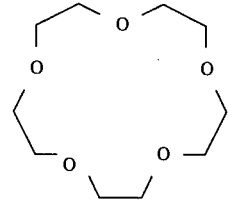
S-4
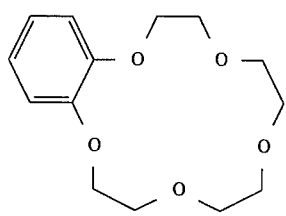
S-5
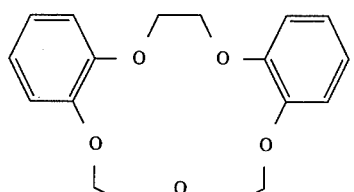
S-6
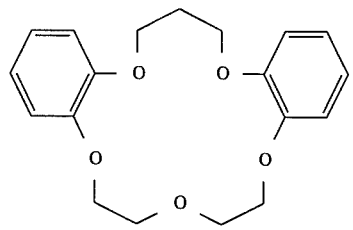
S-7
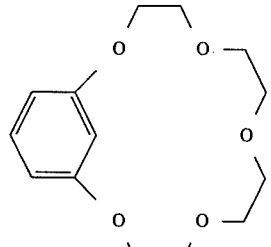
S-8
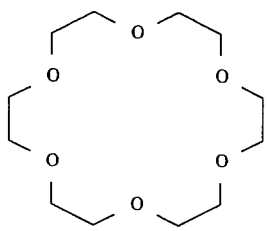
S-9
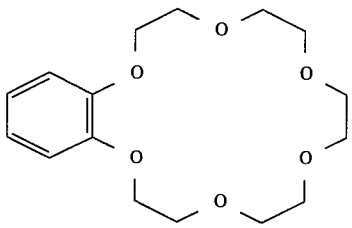
S-10
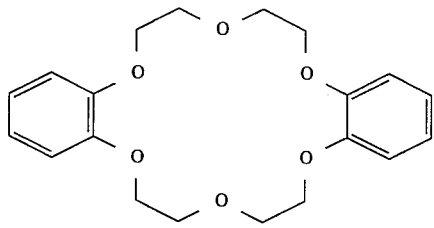
S-11
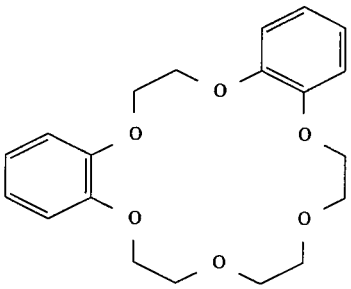
S-12
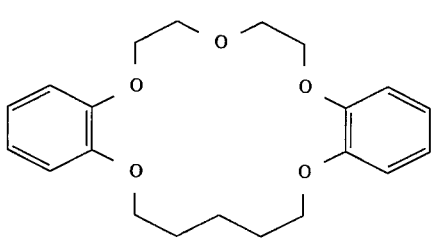
S-13
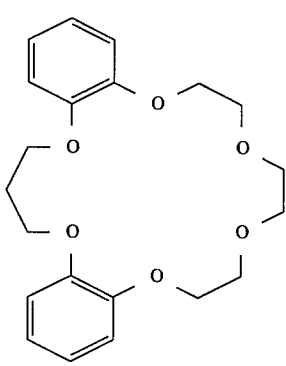
S-14

-continued
S-15
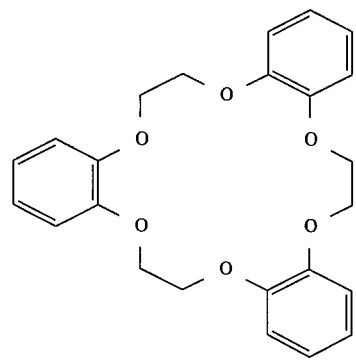
S-16
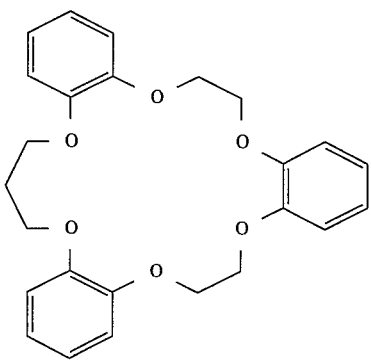
S-17
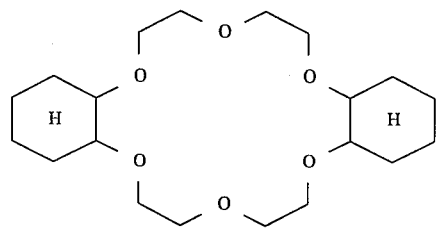
S-18
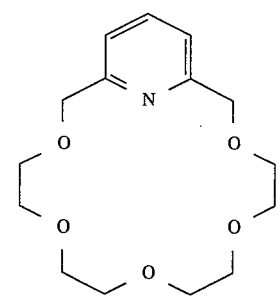
S-19
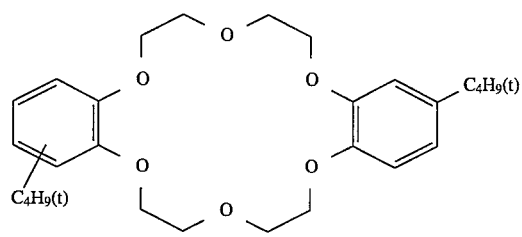
S-20
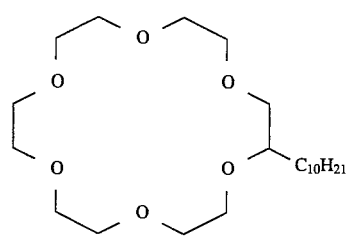
S-21
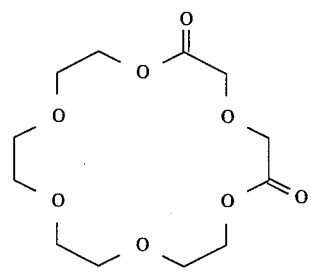
S-22
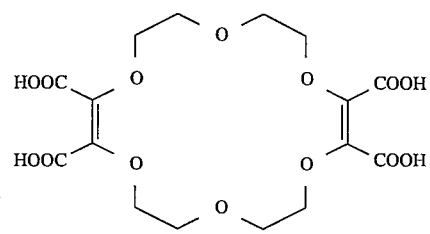
S-23
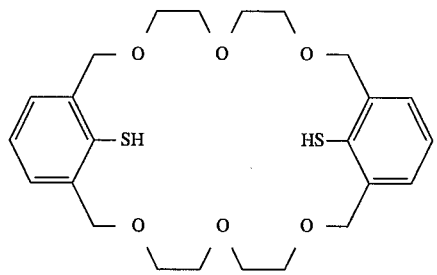
S-24
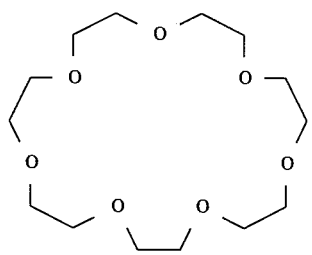
S-25
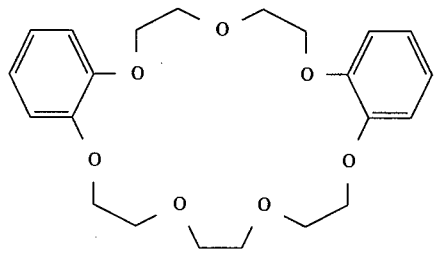
S-26
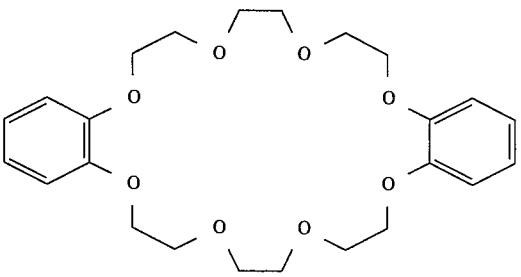

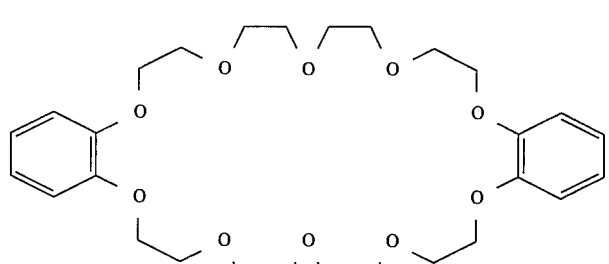
S-27
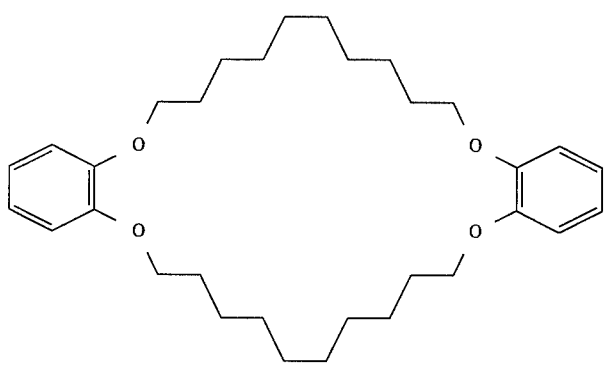
S-28
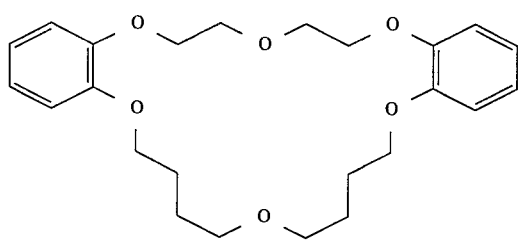
S-29
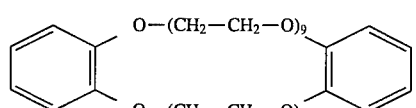
S-30
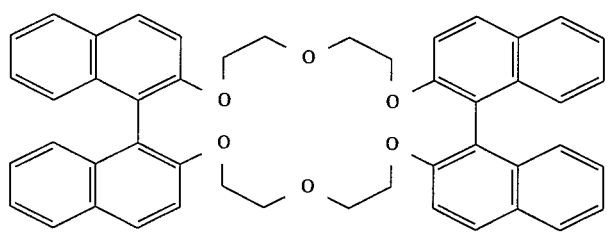
S-31
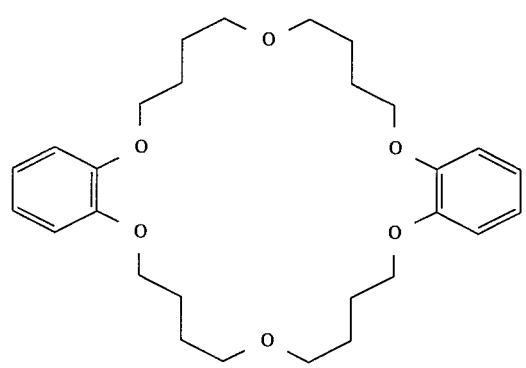
S-32
S-33
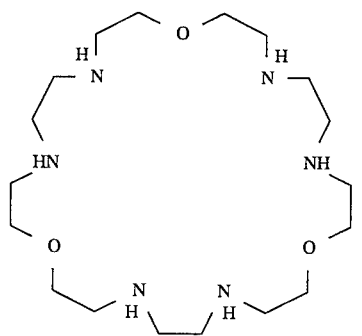
S-34
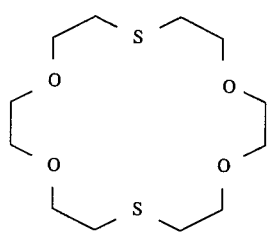
S-35

-continued
S-36
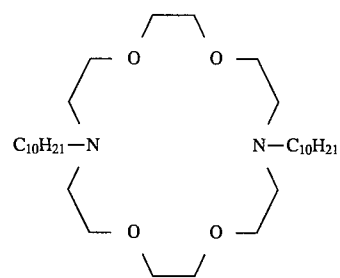
S-37
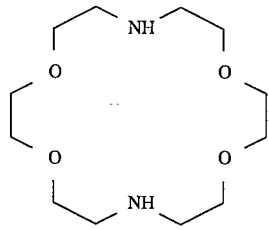
S-38
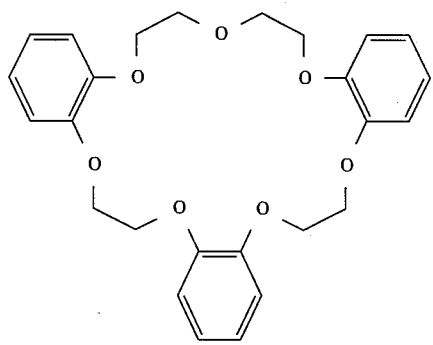
S-39
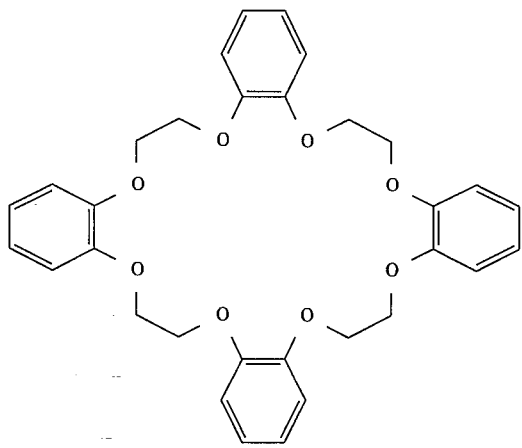
S-40
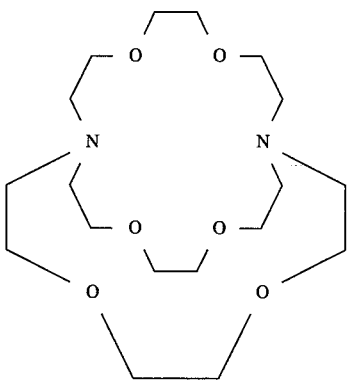
S-41
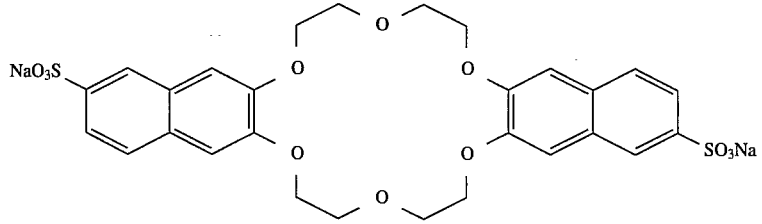
S-42
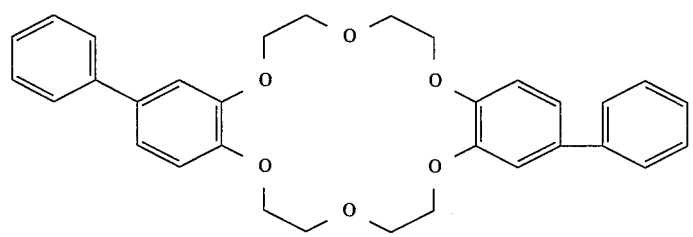

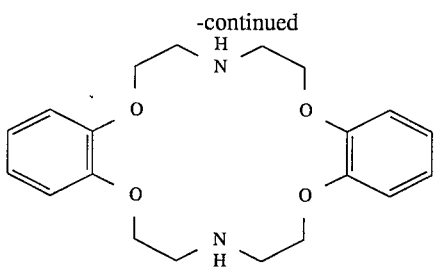

S-43

EXAMPLES

The invention is hereinafter described in detail with the following examples.

EXAMPLE 1

In 600 ml of ethanol were dissolved 200 g of a commercial dibenzo-18-crown-6 (brown powder, product of Nippon Soda Co., Ltd., Lot No. IGG-113) and 65.4 g of potassium acetate. After adding 10 g of active carbon to the solution, the mixture was stirred at room temperature. The insoluble matter was filtered off, and 1,800 ml of water was added to the filtrate, followed by stirring to produce a precipitate. The resulting precipitate was filtered out, washed with water and then with ethanol. Drying of the purified precipitate gave 187 g. of white powder in a yield of 93.5%.

Measurement of Spectral Transmission Factor

In 20-ml measuring flasks was placed 1.00 g of each of the unpurified and purified samples, and ethanol containing 2.0 wt % potassium acetate was added thereto to make up each of them to 20 ml. The spectral transmission factors of the resulting solutions at 660 nm and 440 nm were measured on a spectrophotometer. The results of the measurement are shown in the following Table 1.

TABLE 1

|  | Transmission Factor (%) 660 nm | Transmission Factor (%) 440 nm |
| --- | --- | --- |
| Unpurified Sample | 2.42 | 0.06 |
| Purified Sample | 98.58 | 90.72 |

As is apparent from the table, impurities and coloring were effectively removed by the purification process according to the invention. The yield was as high as 93.5%.

EXAMPLE 2

By processing in the same manner as in Example 1 except that the active carbon was not used, 193 g of grayish white powder was obtained in a yield of 96.5%.

The spectral transmission factors were measured in the same manner as in Example 1; the results are shown in Table 2.

TABLE 2

|  | Transmission Factor (%) 660 nm | Transmission Factor (%) 440 nm |
| --- | --- | --- |
| Unpurified Sample | 2.42 | 0.06 |
| Purified Sample | 97.60 | 88.98 |

It can also be understood from the table that impurities were effectively removed with a yield kept high enough.

Comparative Example 1

From 240 ml of dioxane (a minimum volume necessary for complete dissolution by heating) was recrystallized 20 g of a commercial dibenzo-18-crown-6 (brown powder, product of Nippon Soda Co., Ltd., Lot No. IGG-113).

Obtained was 13.2 g (yield 66%) of yellow needle-like crystals. This low yield indicates that the process of this comparative example is not practical.

Comparative Example 2

From 240 ml of acetonitrile (a minimum volume necessary for complete dissolution by heating) was recrystallized 20 g of a commercial dibenzo-18-crown-6 (brown powder, product of Nippon Soda Co., Ltd., Lot No. IGG-113).

Obtained was 4.84 g (24% yield) of yellow needle-like crystals, showing the impracticability of this process because of a low yield.

EXAMPLE 3

Crown compounds, which had been synthesized according to the process described in J. Am. Chem. Soc., Vol. 89, p. 7017 (1967), were purified in the same manner as in Example 1, except that the salts shown in Table 3 were used in place of the potassium acetate and transmission factors of the purified compounds were measured. The results are shown in Table 3.

TABLE 3

| No. | Illustrated Crown Compound No. | Salts | Transmission Factor (%) of Unpurified One | | Transmission Factor (%) of Purified One | |
| --- | --- | --- | --- | --- | --- | --- |
|  |  |  | 660 nm | 440 nm | 660 nm | 440 nm |
| 1 | S-5 | $CH_3COONa$ | 21.01 | 0.10 | 97.79 | 94.22 |
| 2 | S-9 | $CH_3COOK$ | 13.81 | 4.41 | 98.80 | 95.82 |
| 3 | S-10 | AgSCN | 15.98 | 5.33 | 99.08 | 96.05 |
| 4 | S-15 | KSCN | 18.80 | 8.91 | 99.50 | 96.33 |
| 5 | S-18 | $NH_4SCN$ | 50.01 | 6.76 | 96.34 | 90.89 |
| 6 | S-19 | $CH_3COOK$ | 20.44 | 9.87 | 98.55 | 94.17 |
| 7 | S-34 | KSCN | 80.15 | 38.24 | 93.40 | 91.33 |
| 8 | S-35 | $CH_3COOK$ | 83.29 | 41.01 | 91.90 | 90.38 |
| 9 | S-36 | KSCN | 83.80 | 38.92 | 92.43 | 91.72 |
| 10 | S-40 | KSCN | 77.87 | 63.91 | 94.21 | 92.88 |
| 11 | S-43 | $KI_3$ | 81.13 | 75.06 | 93.34 | 93.01 |

EXAMPLE 4

After adding 8.1 g of sodium thiocyanate to 22.5 g of 15-crown-5 prepared according to the process described in the same J. Am. Chem. Soc. as in Example 3, the crown compound was recrystallized from methanol. The yield was 19.0 g. The resulting white crystals were dissolved in chloroform and washed with water. Removal of the chloroform by distilling gave 13.5 g of 15-crown-5.

Before the purification, the boiling point of the compound was 105° to 109° C. at 0.2 mmHg. This was changed to 108° to 110° C. at 0.2 mmHg after the purification.

This indicates that a crown compound, which is liquid at ordinary temperature, can be safely and effectively purified by the recrystallization according to the invention.

What is claimed is:

1. A process of preparing a purified crown compound with the salt comprising the steps of:
    (a) dissolving a crown compound and a salt in an organic solvent to form a solution of a complex salt of a crown compound;
    (b) filtering the solution to obtain a filtrate;
    (c) adding water to the filtrate to produce a precipitate; and
    (d) filtering out the produced precipitate.

2. The process of claim 1, before the step (b) further comprising the step of adding activated carbon to the solution.

3. The process of claim 1, wherein said crown compound is a crown ether.

4. The process of claim 3, wherein said crown ether has a 12 to 24-membered ring.

5. The process of claim 4, wherein said crown ether has a 15 to 21-membered ring.

6. The process of claim 1, wherein said organic solvent is an alcohol.

7. The process of claim 6, wherein said alcohol comprises methanol, ethanol, n-propanol, n-butanol or iso-propanol.

8. The process of claim 1, wherein said salt is selected from the group consisting of potassium acetate, sodium acetate, ammonium acetate, lithium chloride, silver thiocyanate, sodium thiocyanate and potassium thiocyanate.

9. A process of preparing a purified crown ether having a 12 to 24-membered ring comprising the steps of:
    (a) dissolving a crown ether having a 12 to 24-membered ring and a salt in an alcohol to form a solution of a complex salt of a crown compound, said salt being selected from the group consisting of potassium acetate, sodium acetate, ammonium acetate, lithium chloride, silver thiocyanate, sodium thiocyanate and potassium thiocyanate;
    (b) filtering the solution to obtain a filtrate;
    (c) adding water to the filtrate to produce a precipitate; and
    (d) filtering out the produced precipitate.

10. A process of preparing a purified crown compound comprising the steps of:
    (a) dissolving a crown compound and a salt in a first organic solvent to form a first solution of a complex salt of a crown compound;
    (b) recrystallizing the complex from the first solution to produce a crystal;
    (c) further dissolving the crystal in a second organic solvent to form a second solution;
    (d) adding water to the second solution to produce a precipitate; and
    (e) filtering out the precipitate.

* * * * *

UNITED STATES PATENT AND TRADEMARK OFFICE
CERTIFICATE OF CORRECTION

PATENT NO. : 5,608,058
DATED : March 04, 1997
INVENTOR(S) : Shinri TANAKA et al.

It is certified that error appears in the above-indentified patent and that said Letters Patent is hereby corrected as shown below:

Claim 1, column 13, lines 12-13, after "compound", delete "with the salt".

Claim 1, column 13, line 16, after "compound", insert --with the salt--.

Signed and Sealed this

Eighth Day of July, 1997

Attest:

BRUCE LEHMAN

Attesting Officer

Commissioner of Patents and Trademarks